United States Patent [19]

Seko

[11] Patent Number: 5,597,940

[45] Date of Patent: Jan. 28, 1997

[54] PROCESS FOR PRODUCING β-NITROENAMINE

[75] Inventor: Shinzo Seko, Toyonaka, Japan

[73] Assignee: Sumitomo Chemical Company, Limited, Osaka, Japan

[21] Appl. No.: 401,928

[22] Filed: Mar. 9, 1995

[30] Foreign Application Priority Data

Mar. 16, 1994 [JP] Japan ................. 6-045723
Sep. 5, 1994 [JP] Japan ................. 6-211453
Sep. 9, 1994 [JP] Japan ................. 6-215913
Sep. 14, 1994 [JP] Japan ................. 6-220013

[51] Int. Cl.$^6$ .................. C07C 209/60; C07C 253/30
[52] U.S. Cl. .................. 558/303; 558/304; 564/384; 564/414; 564/462; 564/485; 564/491; 564/509
[58] Field of Search .................. 558/303, 304; 564/509, 384, 414, 485, 462, 491

[56] References Cited

FOREIGN PATENT DOCUMENTS

| | | |
|---|---|---|
| 0254859 | 2/1988 | European Pat. Off. . |
| 0312723 | 4/1989 | European Pat. Off. . |
| 0358047 | 3/1990 | European Pat. Off. . |
| 0616807 | 9/1994 | European Pat. Off. . |
| 0635483 | 1/1995 | European Pat. Off. . |
| 0672646 | 9/1995 | European Pat. Off. . |
| 06043382 | 6/1994 | Japan . |

OTHER PUBLICATIONS

Iimori et al, Tetrahedron Letters, (1979), pp. 2525–2528.
J. Am., Chem., Soc., 78, 1956 *The Structure of β–Amino* . . . By Jeremiah P. Freeman and William D. Emmons, pp. 3405–3408.
Tokumitsu et al, Nippon Kagaku Kaishi, 1983, pp. 88–93 (abstract).
Rajappa, Tetrahedron, (1981), pp. 1453–1480.
*Journal of the American Chemical Society*, vol. 75, No. 1, 14 Jan. 1953 DC US, pp. 285–288, Charles D. Hurd et al., The addition of hydroxylamine to omega–nitrostyrene . . . .
*Journal of the American Chemical Society*, vol. 78, No. 13 7 Jul. 1956 DC US, pp. 3405–3408, Jermiah P. Freeman et al. The structure of Beta–Amino Derivatives . . . .
'Houben–Weyl "Methoden der organischen Chemie" vol. X/1, Part 1, 1971', George Thieme Verlag, Stuttgart, pp. 399 and 1118.

*Primary Examiner*—Joseph McKane
*Assistant Examiner*—Jane C. Oswecki
*Attorney, Agent, or Firm*—Birch, Stewart, Kolasch & Birch, LLP

[57] ABSTRACT

Disclosed is a process for producing β-nitroenamine represented by the formula I:

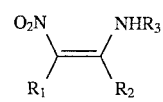

wherein $R_1$ and $R_2$ are the same or different and independently indicate a hydrogen atom or a $C_1$–$C_{10}$ alkyl group which may be optionally substituted with at least one group selected from the group consisting of a halogen atom, a lower alkoxy group, an aryloxy group, a hydroxyl group or an aryl group, or an aryl group which may be optionally substituted with a halogen atom, a lower alkyl group, a lower alkoxy group, an aryl group, an aryloxy group, a nitro group, a cyano group, an acylamino group, a di-lower alkylamino group, an arylamino group, a hydroxyl group, an arylsulfonyl group, a mercapto group, a lower alkylthio group or an arylthio group, $R_1$ and $R_2$ may bond together to form a cycloalkyl or bicycloalkyl and $R_3$ is a hydrogen atom, a lower alkyl group, a cycloalkyl group or an aralkyl group; and an intermediate for producing the β-nitroenamine.

14 Claims, No Drawings

PROCESS FOR PRODUCING β-NITROENAMINE

FIELD OF THE INVENTION

The present invention relates to a novel process for producing β-nitroenamine and an intermediate thereof.

BACKGROUND OF THE INVENTION

Heretofore, β-nitroenamine has been known as a unique and important compound having the reactivities of both enamine and nitroolefin. Also, it is known as a basic structure of agricultural insecticides and is an extremely important compound as an intermediate of medicines and agrochemicals because of its easy derivation to various heterocycles. As the production process thereof, there have been known various methods such as condensation of α-nitrocarbonyl compound with an amine in the presence or absence of titanium tetrachloride catalyst [see J. Am. Chem. Soc., Vol. 78,3405 (1956); Nippon Kagaku Kaishi, 88 (1983)], substitution reaction of nitroolefins containing a good leaving group (e.g. a halogen, an alkoxyl, an alkylthio, a nitro, an amino group, etc.) at its β-position with an amine [see Tetrahedron, Vol. 37,1453 (1981)], condensation of ethyl cyanoformate with nitromethane [see Tetrahedron Letters, 2525 (1979)] and the like.

However, each of the method described above is disadvantageous in that the reaction yield is low or preparation of the starting material is difficult or other disadvantages. Therefore, it has been desired to synthesize β-nitroenamine simply in good yield from easily available compounds.

OBJECTS OF THE INVENTION

Under these circumstances, the present inventor has intensively studied a process for producing β-nitroenamine easily in good yield, the operation of the process being simple. As a result, it has been found that, by means of reacting readily available and simple nitroolefin containing no leaving group at the β-position and a hydroxylamine derivative or a salt thereof in the presence of a base, β-nitroenamine can be obtained directly in good yield. Further, it has also been found that, by treating a N-(β-nitroethyl)hydroxylamine derivative, which can be obtained quantitatively from the corresponding nitroolefin and hydroxylamine derivative, with a base, β-nitroenamine can also be obtained in good yield, thus the present invention has been accomplished.

That is, one object of the present invention is to provide a process for producing β-nitroenamine directly from simple nitroolefin in good yield.

Another object of the present invention is to provide an intermediate for β-nitroenamine.

These objects as well as other objects and advantages of the present invention will become apparent to those skilled in the art from the following description..

SUMMARY OF THE INVENTION

The present invention provide;
1. a process for producing β-nitroenamine represented by the formula I:

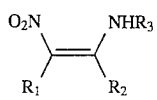

wherein $R_1$ and $R_2$ are the same or different and independently indicate a hydrogen atom or a straight-chain or branced $C_1$–$C_{10}$ alkyl group which may be optionally substituted with at least one group selected from the group consisting of a halogen atom, a lower alkoxy group, an aryloxy group, hydroxyl group or an aryl group, or an aryl group which may be optionally substituted with at least one group selected from the group consisting of a halogen atom, a lower alkyl group, a lower alkoxy group, an aryl group, an aryloxy group, a nitro group, a cyano group, an acylamino group, a lower dialkylamino group, an arylamino group, a hydroxyl group, an arylsulfonyl group, a mercapto group, a lower alkylthio group or an arylthio group; and $R_1$ and $R_2$ may bond together to form a cycloalkyl or bicycloalkyl group; and $R_3$ is a hydrogen atom, a lower alkyl group, a cycloalkyl group or an aralkyl group, which comprises reacting a nitroolefin of the formula II:

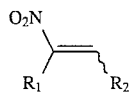

wherein $R_1$ and $R_2$ are as defined above, with a hydroxylamine derivative of the formula III:

wherein $R_3$ is the same as defined above and $R_4$ is a lower alkyl group or an aralkyl group, or a salt thereof in the presence of a base;

2. a process for producing β-nitroenamine represented by the formula I:

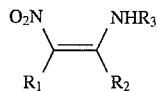

wherein $R_1$, $R_2$ and $R_3$ are as defined above, which comprises reacting an N-(β-nitroethyl) hydroxylamine derivative of the formula IV:

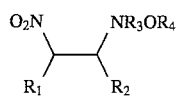

wherein $R_1$, $R_2$, $R_3$ and $R_4$ are as defined above, with a base;

3. a process for producing β-nitroenamine represented by the formula I:

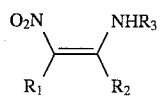

wherein $R_1$, $R_2$ and $R_3$ are as defined above, which comprises the steps of;
(a) reacting a nitroolefin of the formula II:

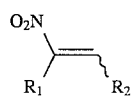

wherein $R_1$ and $R_2$ are as defined above with a hydroxylamine derivative of the formula III:

wherein $R_3$ and $R_4$ are as defined above to obtain an N-(β-nitroethyl) hydroxylamine derivative of the formula IV:

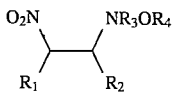

wherein $R_1$, $R_2$, $R_3$ and $R_4$ are as defined above; and then
(b) reacting the resulting derivative with a base;
4. an N-(β-nitroethyl)hydroxylamine derivative represented by the formula IV:

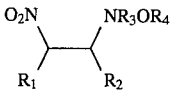

wherein $R_1$, $R_2$, $R_3$ and $R_4$ are as defined above; and
5. a process for producing an N-(β-nitroethyl)hydroxylamine derivative represented by the formula IV:

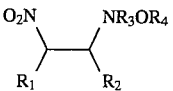

wherein $R_1$, $R_2$, $R_3$ and $R_4$ are as defined above, which comprises reacting a nitroolefin of the formula II:

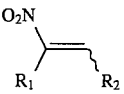

wherein $R_1$ and $R_2$ are as defined above with a hydroxylamine derivative of the formula III:

wherein $R_3$ and $R_4$ are as defined above.

DETAILED DESCRIPTION OF THE INVENTION

Hereinafter, the present invention will be explained in detail.

The compounds used as the raw material of the present invention are represented by the formula II or III. Among the respective substituents of the formulas, "lower alkyl" means a straight-chain or branched $C_1$–$C_4$ alkyl, "lower alkoxyl" means a straight-chain or branched $C_1$–$C_4$ alkoxyl and "aryl" means a monocyclic or polycyclic aromatic carbon ring (e.g. phenyl, naphthyl, anthryl, etc.) or a monocyclic or polycyclic aromatic heterocycle (e.g. furyl, pyrrolyl, thienyl, pyridyl, imidazolyl, triazolyl, quinolyl, etc.), "cycloalkyl" means a $C_3$–$C_6$ cycloalkyl group(e.g. a cyclopropyl group, a cyclopentyl group, a cyclohexyl group), "acylamino" means a $C_2$–$C_4$ alkanoylamino group (e.g. an acetylamino group, a propionylamino group) or a benzoylamino group, and "aralkyl" means a benzyl group or a phenethyl group.

The nitroolefin represented by the formula II can be easily synthesized, for example, by the condensation of an aldehyde with a nitroalkane, elimination of acetic acid from β-nitroacetate [Org. Syn., Coll. Vol. I, 413 (1941); J. Org. Chem., Vol. 15, 8, (1950)], dehydration of β-nitroalcohol [J. Chem. Soc., 1471 (1947)] or the like. Examples thereof include nitroethylene, 1-nitropropene, 2-nitropropene, 2-nitro-1-butene, 1-nitro-1-butene, 2-nitro-2-butene, 2-nitro-1-pentene, 1-nitro-1-pentene, 2-nitro-2-pentene, 3-nitro-2-pentene, 1-nitro-1-octene, 1-nitro-1-nonene, 1-nitro-1-decene, 1-nitro-1-dodecene, 2-methyl-4-nitro-3-hexene, 5-methoxy-2-nitro-2-hexene, 5-chloro-2-nitro-2-hexene, 5-phenoxy-2-nitro-2-hexene, 5-hydroxy-2-nitro-2-hexene,1-nitro3-phenylpropene, β-nitrostyrene, 4-methyl-β-nitrostyrene, 3-nitro-β-nitrostyrene, 1-phenyl-2-nitropropene, α-nitrostilbene, 1-(3-methoxyphenyl)-2-nitropropene, 1-(2,3-dimethoxyphenyl)-2-nitropropene, 1-(3-chlorophenyl)-2-nitropropene, 1-(3-hydroxyphenyl)-2-nitropropene, 1-(3-nitrophenyl)-2-nitropropene, 1-(3-phenylphenyl)-2-nitropropene, 1-[3-(1H-imidazol-1yl)phenyl]-2-nitropropene, 1-[3-(1H-1,2,4-triazol-1-yl)phenyl]-2-nitropropene, 1-(3-phenoxyphenyl)-2-nitropropene, 1-(3-cyanophenyl)-2-nitropropene, 1-(3-acetamidophenyl)-2-nitropropene, 1-(3-dimethylaminophenyl)-2-nitropropene, 1-(3-anilinophenyl)-2-nitropropene, 3-(β-methyl-β-nitrovinyl) diphenylsulfone, 1-(3-mercaptophenyl)-2-nitropropene, 1-(3-methylthiophenyl)-2-nitropropene, 3-(β-methyl-β-nitrovinyl)diphenylsulfide, 1-(2-furyl)-2-nitropropene, 1-(2-pyridyl)-2-nitropropene, 1-(2-pyrrolyl)-2-nitropropene, 1-(2-thienyl)-2-nitropropene, 1-(2-naphthyl)-2-nitropropene, 1-(2-quinolyl)-2-nitropropene, 1-nitrocyclohexene, 3-methyl-1-nitrocyclohexene, 1-nitrocyclopentene, 2-nitronorbornene and the like.

Examples of the hydroxylamine derivative represented by the formula III include O-methylhydroxylamine, O-ethylhydroxylamine, O-t-butylhydroxylamine, O-benzylhydroxylamine, N,O-dimethylhydroxylamine, N-cyclohexyl-O-methylhydroxylamine, N-benzyl-O-methylhydroxylamine and the like. Among them, O-methylhydroxylamine is most suitable.

The hydroxylamine derivative can be used in the form of a salt, i.e. inorganic acid salts such as hydrochloride, sulfate, etc, but it is preferred to use as it is.

The base to be used is not particularly limited. For example, there can be suitably used alkali metal hydroxides, alkali metal hydrides, alkali metal amides, alkali metal alkoxides and the like.

Examples of the base include an alkali metal hydroxide such as sodium hydroxide or potassium hydroxide; an alkali metal hydride such as sodium hydride; an alkali metal amide such as sodium amide, or lithium diisopropylamide, an alkali metal alkoxide such as sodium methoxide, sodium ethoxide, potassium t-butoxide and the like.

The hydroxylamine derivative or a salt thereof may be usually used in an amount of from 0.5 to 6 moles, preferably from 1 to 3 moles per mole of the nitroolefin as the starting material.

Further, the base may be usually used in an amount of from 0.1 to 6, preferably from 2 to 5 moles per mole of the nitroolefin.

A solvent is normally used for the reaction. As the solvent, for example, there can be used an aprotic solvent which includes an aprotic polar solvent such as N, N-dimethylformamide, dimethyl sulfoxide, etc.; ether solvents such as ethylene glycol dimethyl ether, diethylene glycol dimethyl ether, 1,4-dioxane, tetrahydrofuran, etc.; aromatic solvents such as benzene, toluene, chlorobenzene, etc.; aliphatic hydrocarbon solvents such as hexane, heptane, etc.; alcohol solvents; such as t-butanol, etc.; or a mixed solvent thereof.

The solvent is normally used in an amount of from 1 to 100 times amount by weight of the nitroolefin as the starting material.

The reaction temperature is normally within a range of from −40° to 100° C., preferably from 0° to 50° C.

The reaction method is not particularly limited, but a method wherein a mixture of the nitroolefin and the hydroxylamine derivative is added dropwise to a solution of a base is normally preferred.

An exothermic reaction may occur by only mixing the nitroolefin and hydroxylamine derivatives depending on the kind of the starting material. The β-nitroenamine obtained can be easily isolated and purified from the reaction mixture after the completion of the reaction by a normal procedure, e.g. distillation, extraction, recrystallization, various chromatographies or the like.

The β-nitroenamine I can be easily obtained even by reacting the N-(β-nitroethyl) hydroxylamine derivative IV with a base. In this reaction the same base, solvent and reaction conditions as used for the above-described process and also similar post-treatment can be employed. The amount of the base to be used is usually from 0.1 to 6 moles, preferably from 2 to 5 moles per mole of the N-(β-nitroethyl) hydroxylamine derivative IV.

Examples of the N-(β-nitroethyl)hydroxylamine derivative include O-methyl-N-(β-nitroethyl)hydroxylamine, O-methyl-N-(β-nitropropyl)hydroxylamine, O-ethyl-N-(β-nitropropyl)hydroxylamine, O-t-butyl-N-(β-nitropropyl)hydroxylamine, O-benzyl-N-(β-nitropropyl)hydroxylamine, N, O-dimethyl-N-(β-nitropropyl) hydroxylamine, O-methyl-N-(α-methyl-β-nitroethyl) hydroxylamine, O-methyl-N-(β-nitrobutyl)hydroxylamine, O-methyl-N-(α-methyl-β-nitropropyl) hydroxylamine, O-methyl-N-[α-(nitromethyl) propyl] hydroxylamine, O-methyl-N-(β-nitropentyl)hydroxylamine, O-methyl-N-[α-(nitromethyl)butyl]hydroxylamine, N-(α-ethyl-β-nitropropyl)-O-methylhydroxylamine, O-methyl-N-(α-methyl-β-nitrobutyl) hydroxylamine, O-methyl-N-α-(nitromethyl)heptyl]hydroxylamine, O-methyl-N-[α-(nitromethyl) octyl]hydroxylamine, O-methyl-N-[α-(nitromethyl)nonyl]hydroxylamine, O-methyl-N-[α-(nitromethyl)undecyl]hydroxylamine, N-(α-isopropyl-β-nitrobutyl)-O-methylhydroxylamine, O-methyl-N-(α-nitromethyl-β-phenylethyl) hydroxylamine, O-methyl-N-[1-(α-nitroethyl)-3-methoxybutyl]hydroxylamine, O-methyl-N-[1-(α-nitroethyl)-3-phenoxybutyl]hydroxylamine, O-methyl-N-[1-(α-nitroethyl)-3-chlorobutyl] hydroxylamine, O-methyl-N-(β-nitro-α-phenylethyl) hydroxylamine, O-methyl-N-(β-nitro-α-phenylpropyl)hydroxylamine, O-methyl-N-(α, β-diphenyl-β-nitroethyl) hydroxylamine, O-methyl-N-[1-(3-chlorophenyl)-2-nitropropyl]hydroxylamine, O-methyl-N-[2-nitro-1-(p-tolyl)ethyl] hydroxylamine, O-methyl-N-[1-(3-methoxyphenyl)-2-nitropropyl]hydroxylamine, O-methyl-N-[1-(2,3-dimethoxyphenyl)-2-nitropropyl]hydroxylamine, O-methyl-N-[1-(3-nitrophenyl)-2-nitroethyl]hydroxylamine, O-methyl-N-[1-(3-cyanophenyl)-2-nitropropyl]hydroxylamine, O-methyl-N-(β-nitrocyclohexyl) hydroxylamine, O-methyl-N-(2-methyl-6-nitrocyclohexyl) hydroxylamine, O-methyl-N-(β-nitrocyclopentyl)hydroxylamine, O-methyl-N-(3-nitronorbornan-2-yl) hydroxylamine and the like.

The N-(β-nitroethyl)hydroxylamine derivative can be produced, easily and almost quantitatively, by reacting the nitroolefin of the formula II with the hydroxylamine derivative of the formula III.

No other reaction reagent is usually required for conducting this reaction and both of the starting compounds may only be mixed, but the mixture may be heated if necessary to cause the reaction to proceed. In this reaction, the hydroxylamine derivative may be normally used in amount of from 0.5 to 6 moles, preferably from 1 to 3 moles per mole of the nitroolefin II.

A reaction solvent may be used in the reaction.

When using a solvent, the solvent is not particularly limited if it is inert to the reaction. As the solvent, for example, there can be used an aprotic solvent which includes aprotic polar solvent such as N,N-dimethylformamide, dimethyl sulfoxide, etc.; ether solvents such as diethyl ether, ethylene glycol dimethyl ether, diethylene glycol dimethyl ether, 1,4-dioxane, tetrahydrofuran, etc.; halogenated solvents such as dichloromethane, 1,2-dichloroethane, chlorobenzene, etc.; aromatic hydrocarbon solvents such as benzene, toluene, xylene, etc.; aliphatic hydrocarbon solvents such as hexane, heptane, etc.; alcohol solvents such as methanol, ethanol, t-butanol, etc.; and a mixture thereof.

Also, in this reaction, the reaction temperature is normally within a range of from −40° to 100° C., preferably from 0° to 70° C.

The N-(β-nitroethyl)hydroxylamine derivative of the formula IV can be easily produced by this reaction, and the derivative can be easily isolated and purified from the reaction mixture after the completion of the reaction by a normal operation such as recrystallization, distillation, various chromatographies and/or the like. Further, the reaction mixture obtained after completion of the reaction can also be used as it is for the production of β-nitroenamine in the next step.

As described above, according to the process of the present invention, β-nitroenamine can be produced from a simple nitroolefin, which can be easily available industrially, in good yield.

Further, it is also possible to produce β-nitroenamine by reacting an O-substituted-N-(β-nitroethyl) hydroxylamine derivative, which is formed as an intermediate, with a base.

The hydroxylamine derivative or a salt thereof of the formula III used as a new amination reagent in the present invention can be easily produced from hydroxylamine at rather low cost so that the process of the present invention is significantly advantageous industrially.

EXAMPLES

The following Examples further illustrate the present invention in detail but are not to be construed to limit the scope thereof.

EXAMPLE 1

1-Nitrocyclohexene (254 mg, 2 mmol) and O-methylhydroxylamine (118 mg, 2.5 mmol) were dissolved in 2 ml of N,N-dimethylformamide, and the mixture was added dropwise to 8 ml of N,N-dimethylformamide solution containing potassium t-butoxide (673 mg, 6 mmol) at 25° C. over 5 minutes. After the completion of the dropwise addition, the resulting mixture was stirred at 25° C. for 10 minutes and then an aqueous saturated ammonium chloride solution was added to the reaction mixture, followed by extraction with methylene chloride.

The resulting organic layer was dried over anhydrous magnesium sulfate and, after the solvent was distilled off, the product was isolated and purified by silica gel thin-layer chromatography (eluent: ethyl acetate/hexane=1/1) to give 1-amino-2-nitrocyclohexene (yield: 91%).

$^1$H NMR spectrum (CDCl$_3$, 270 MHz)

δ1.63–1.78 (m, 4H), 2.53 (t, 2H, J=6.27 Hz), 2.62 (t, 2H, J=6.27 Hz), 6.73 (br.s, 1H), 9.69 (br.s, 1H)

$^{13}$C NMR spectrum (CDCl$_3$, 68 MHz)

δ21.12, 22.41, 24.87, 30.64, 118.46, 158.26

Mass spectrum (EI-MS)
m/z 142 (M+), 125, 109, 107, 95, 84, 77, 67, 56, 54

EXAMPLES 2 to 10

According to the same manner as that described in Example 1 except for using a nitroolefin containing various substituents shown in Table 1 (2 mmol each) in place of 1-nitrocyclohexene, the reaction and post treatment were conducted and the resulting product was isolated and purified to give the corresponding β-nitroenamines in yield shown in Table 1.

In Example 9, potassium t-butoxide (10 mmol) was used. Further, the reaction was monitored with silica gel thin-layer chromatography until the disappearance of the starting material was confirmed in all Examples.

In case where the resulting β-nitroenamine is unstable in water (Examples 2, 3, 4 and 10), the reaction mixture after the completion of the reaction was allowed to pass through a silica gel short column without addition of an aqueous saturated ammonium chloride solution and the following extraction with methylene chloride and, after the solvent was distilled off, the product was isolated and purified by silica gel thin-layer chromatography.

TABLE 1

$$\underset{R_1}{\overset{O_2N}{\diagdown}}=\underset{R_2}{\diagup} + NH_2OMe \longrightarrow \underset{R_1}{\overset{O_2N}{\diagdown}}\underset{R_2}{\overset{NH_2}{\diagup}}$$

| Example No. | R₁ | R₂ | Yield (%) |
|---|---|---|---|
| 2 | Me | H | 61 |
| 3 | Me | Me | 78 |
| 4 | H | n-Hexyl | 87 |
| 5 | H | Ph | 94 |
| 6 | H | m-NO₂—C₆H₄ | 75 |
| 7 | Me | m-Cl—C₆H₄ | 56 |
| 8 | Me | m-MeO—C₆H₄ | 59 |
| 9 | Me | m-HO-C6H4 | 31 |
| 10 | Me | 2-Furyl | 30 |

The analysis values of ¹H NMR spectrum, ¹³C NMR spectrum and mass spectrum of β-nitroenamine obtained in the above Examples will be shown below.

(Z)-1-amino-2-nitropene (Example 2)
¹H NMR spectrum (CDCl₃, 270 MHz)
δ 2.07 (s, 3H), 6.03 (br.s, 1H), 7.02 (t, 1H, J=11.55 Hz), 8.62 (br.s, 1H)
¹³C NMR spectrum (CDCl₃, 68 MHz)
δ 16.14, 118.45, 143.85
Mass spectrum (EI-MS)
m/z 102 (M+), 84, 72, 54

(Z)-2-amino-3-nitro-2-butene (Example 3)
¹H NMR spectrum (CDCl₃, 270 MHz)
δ 2.12 (s, 3H), 2.18 (s, 3H), 7.94 (br.s, 1H), 10.08 (br.s, 1H)
¹³C NMR spectrum (CDCl₁₃, 68 MHz)
δ 13.70, 21.39, 115.92, 158.24
Mass spectrum (EI-MS)
m/z 116 (M+), 99, 86, 69, 58, 54, 42

(Z)-2-amino-1-nitro-1-octene (Example 4)
¹H NMR spectrum (CDCl₃, 270 MHz)
δ 0.89 (m, 3H), 1.30 (m, 6H), 1.61 (m, 2H), 2.24 (m, 2H), 6.54 (d, 1H, J=0.90 Hz), 6.67 (br.s, 1H), 9.22 (br.s, 1H)
¹³C NMR spectrum (CDCl₃, 68 MHz)
δ13.86, 22.30, 27.85, 28.50, 31.23, 34.16, 110.30, 162.19
Mass spectrum (EI-MS)
m/z 172 (M+), 126, 115, 102, 96, 82, 70, 56, 41

(Z)-α-amino-β-nitrostyrene (Example 5)
¹H NMR spectrum (CDCl₃, 270 MHz)
δ 6.64 (br.s, 1H), 6.81 (s, 1H), 7.45–7.59 (m,5H), 9.29 (br.s, 1H)
3C NMR spectrum (CDCl₁₃, 68 MHz)
δ 110.60, 126.52, 129.22, 131.81, 133.32, 157.70
Mass spectrum (EI-MS)
m/z 164 (M+), 134, 117, 104, 91, 77, 65, 63, 51

(Z)-3-nitro-α-amino-β-nitrostyrene (Example 6)
¹H NMR spectrum (d₆-DMSO, 400 MHz)
δ 6.93 (s, 1H), 7.79 (t, 1H, J=8.05Hz), 8.09 (m, 1H), 8.40(m, 1H), 8.45 (m, 1H ) 9.09 (br.s, 1H), 9.38 (br.s, 1H)
¹³C NMR spectrum (d₆–DMSO, 100 MHz)
δ109.70, 122.55, 125.91, 130.49, 134.00, 134.65, 147.74, 155.76
Mass spectrum (FD-MS)
m/z 209 (M+)

(Z)-1-amino-1-(3-chlorophenyl)-2-nitropropene (Example 7)
¹H NMR spectrum (CDCl₃, 400 MHz)
δ 1.96 (s, 3H), 5.72 (br.s, 1H), 7.29 (td, 1H, J=1.51Hz, 7.39Hz), 7.39–7.50 (m,3H), 9.56 (br.s, 1H)
¹³C NMR spectrum (CDCl₃, 100 MHz)
δ 15.63, 118.36, 125.65, 127.50, 130.36, 130.39, 134.96, 137.68, 154.84
Mass spectrum (FD-MS)
m/z 212 (M+)

(Z)-1-amino-1-(3-methoxyphenyl)-2-nitropropene (Example 8)
¹H NMR spectrum (CDCl₃, 270 MHz)
δ 1.96, (s, 3H), 3.84 (s, 3H), 6.00 (br.s, 1H), 6.89–7.03 (m, 3H), 7.38 (t, 1H, J=7.92Hz), 9.69 (br.s, 1H)
¹³C NMR spectrum (CDCl₃, 68 MHz)
δ 15.67, 55.35, 112.94, 115.63, 117.88, 119.46, 130.06, 137.18, 157.03, 159.64
Mass spectrum (FD-MS)
m/z 208 (M+)

(Z)-1-amino-1-(3-hydroxphenyl)-2-nitropropene (Example 9)
¹H NMR spectrum (d₆-DMSO, 270 MHz)
δ 1.85 (s, 3H), 6.79–6.93 (m, 3H), 7.31 (t, 1H, J=7.92 Hz), 8.72 (br.s, 1H), 9.83 (br.s, 1H)
δ ¹³C NMR spectrum (d₆-DMSO, 68 MHz)
δ 15.78, 114.43, 115.38, 116.84, 118.17, 129.81,136.91, 157.41,159.17
Mass spectrum (FD-MS)
m/z 194 (M+)

(Z)-1-amino-1-(2-furyl)-2-nitropropene (Example 10)
¹H NMR spectrum (CDCl₃, 270 MHz)
δ 2.39 (s, 3H), 6.62 (dd, 1H, J=1.65 Hz, 3.63 Hz), 6.89 (d, 1H, J=3.63 Hz), 7.65 (d, 1H, J=1.65 Hz), NH₂ n.d.
3C NMR spectrum (CDCl₃, 68 MHz)
δ 15.56, 112.62, 116.82, 117.68, 145.10, 145.23, 146.29
Mass spectrum (FD-MS)
m/z 168 (M+)

EXAMPLE 11 trans-β-Nitrostyrene (149 mg, 1 mmol) and N,O-dimethylhydroxylamine (76 mg, 1.25 mmol) were dissolved in 2 ml of N,N-dimethylformamide, and the mixture was added dropwise to 3 ml of N,N-dimethylformamide solution containing potassium t-butoxide (336 mg, 3 mmol) at 25° C. over 5 minutes. After the completion of the dropwise addition, the resulting mixture was stirred at 25° C. for 10 minutes and then an aqueous saturated ammonium chloride solution was added to the reaction mixture, follwed by extraction with methylene chloride.

The resulting organic layer was dried over anhydrous magnesium sulfate and, after the solvent was distilled off, the product was isolated and purified by silica gel thin-layer chromatography (eluent: ethyl acetate/hexane=1/1) to give (Z)-α-methylamino-β-nitrostyrene (yield: 51%).
$^1$H NMR spectrum (CDCl$_3$, 270 MHz)
δ 2.99 (d, 3H, J=5.61 Hz), 6.58 (s, 1H), 7.34–7.39 (m, 2H), 7.47–7.54 (m, 3H), 1.022 (br.s, 1H)
$^{13}$C NMR spectrum (CDCl$_3$, 68 MHz)
δ 32.29, 111.61, 128.03, 129.34, 131.07, 131.43, 161.60
Mass spectrum (FD-MS)
m/z 178 (M$^+$)

EXAMPLE 12

O-Methylhydroxylamine (236 mg, 5 mmol) was added dropwise to N,N-dimethylformamide (2 ml) solution of 2-nitropropene (348 mg, 4 mmol). After stirring at 25° C. for 10 minutes, water was added and the extraction was conducted with methylene chloride.

The resulting organic layer was sufficiently washed with water and dried over anhydrous magnesium sulfate and, after the solvent was distilled off, the product was isolated and purified by silica gel thin-layer chromatography (eluent: ethyl acetate/hexane=1/5).
O-Methyl-N-(β-nitropropyl)hydroxylamine (yield: 90%)
$^1$H NMR spectrum (CDCl$_3$, 270 MHz)
δ 1.55 (d, 3H, J=6.93Hz), 3.18 (m, 1H), 3.40 (m, 1H), 3.52 (s, 3H), 4.89 (m, 1H) 5.78 (br.s, 1H)
Mass spectrum (EI-MS)
m/z 134 (M$^+$), 87, 72, 60, 56, 46, 41

O-Methyl-N-(β-nitropropyl)hydroxylamine (268 mg, 2 mmol) thus obtained was dissolved in 2 ml of N,N-dimethylformamide, and the solution was added dropwise to 3 ml of N,N-dimethylformamide solution containing potassium t-butoxide (673 mg, 6 mmol) at 25° C. over 5 minutes. After the completion of the dropwise addition, the resulting mixture was stirred at 25° C. for 10 minutes and allowed to pass through a silica gel short column (eluent: ethyl acetate).

After the solvent was distilled off, the product was isolated and purified by silica gel thin-layer chromatography (eluent: ethyl acetate/hexane=1/1) to give 1-amino-2-nitropropene (yield: 61%).

EXAMPLE 13

O-Methylhydroxylamine (176 mg, 3.75 mmol) was added to (E)-2-nitro-2-butene (303 mg, 3 mmol) and the resulting mixture was stirred at 25° C. for 10 minutes. Then, the product was isolated and purified by silica gel thin-layer chromatography (eluent: ethyl acetate/hexane=1/5). O-Methyl-N-(α-methyl-β-nitropropyl)hydroxylamine (mixture of diastereomers, yield: 95%)
Diastereomer (1)
$^1$H NMR spectrum (CDCl$_3$, 270 MHz)
δ 1.07 (d, 3H, J=6.27 Hz), 1.54 (d, 3H, J=6.27 Hz), 3.44 (m, 1H), 3.53 (s, 3H), 4.86 (m, 1H), 5.62 (br.s, 1H)
Mass spectrum (EI-MS)
m/z 148 (M$^+$), 102, 86, 74, 56, 42
Diastereomer (2)
$^1$H NMR spectrum (CDCl$_3$, 270 MHz)
δ1.11 (d, 3H, J=7.26 Hz), 1.52 (d, 3H, J=6.27Hz), 3.57 (m, 1H), 4.76 (m,1H), 5.62 (br.s, 1H)
Mass spectrum (EI-MS)
m/z 148 (M$^+$), 103, 101, 86, 74, 56, 42

O-Methyl-N-(α-methyl-β-nitropropyl)hydroxylamine (mixture of diastereomers, 148 mg, 1 mmol) thus obtained was dissolved in 2 ml of N,N-dimethylformamide, and the solution was added dropwise to 3 ml of N,N-dimethylformamide solution containing potassium t-butoxide (224 mg, 2 mmol) at 25° C. over 5 minutes. After the completion of the dropwise addition, the resulting mixture was stirred at 25° C. for 10 minutes and allowed to pass through a silica gel short column (eluent: ethyl acetate).

After the solvent was distilled off, the product was isolated and purified by silica gel thin-layer chromatography (eluent: ethyl acetate/hexane=1/1) to give (Z)-2-amino-3-nitro-2-butene (yield: 80%).

EXAMPLE 14

O-Methylhydroxylamine (176 mg, 3.75 mmol) was added dropwise to a methylene chloride (1 ml) solution of (E)-1-nitro-1-octene (471 mg, 3 mmol) and the mixture was stirred at 25° C. for 10 minutes. Then, the product was isolated and purified by silica gel thin-layer chromatography (eluent: ethyl acetate/hexane=1/10).
O-Methyl-N-[α-(nitromethyl)heptyl]hydroxylamine (yield: 100%)
$^1$H NMR spectrum (CDCl$_3$, 270 MHz)
δ 0.89 (m, 3H), 1.26–1.56 (m, 10H), 3.52 (m, 1H), 3.52 (s, 3H), 4.43 (dd, 1H, J=4.29 Hz, 12.54 Hz), 4.58 (dd, 1H, J=7.26 Hz, 12.54 Hz), 5.76 (br.s, 1H)
$^{13}$C NMR spectrum (CDCl$_3$, 68 MHz)
δ14.25, 22.79, 26.13, 29.33, 29.47, 31.83, 59.30, 62.72, 76.87
Mass spectrum (EI-MS)
m/z 204 (M$^+$), 173, 160, 144, 126, 119, 100, 87, 73, 72, 55, 41

O-Methyl-N-[α-(nitromethyl)heptyl]hydroxylamine (204 mg, 1 mmol) thus obtained was dissolved in 2 ml of N,N-dimethylformamide, and the solution was added dropwise to 3 ml of N,N-dimethylformamide solution containing potassium t-butoxide (336 mg, 3 mmol) at 25° C. over 5 minutes. After the completion of the dropwise addition, the resulting mixture was stirred at 25° C. for 60 minutes and allowed to pass through a silica gel short column (eluent: ethyl acetate).

After the solvent was distilled off, the product was isolated and purified by silica gel thin-layer chromatography (eluent: ethyl acetate/hexane=1/1) to give (Z)-2-amino-1-nitro-1-octene (yield: 87%).

EXAMPLE 15

O-Methylhydroxylamine (176 mg, 3.75 mmol) was added to 1-nitrocyclohexene (382 mg, 3 mmol) and the resulting mixture was stirred at 25° C. for 60 minutes. Then, the product was isolated and purified by silica gel thin-layer chromatography (eluent: ethyl acetate/hexane=1/5).
O-Methyl-N-(β-nitrocyclohexyl)hydroxylamine (mixture of diastereomers, yield: 100%)
Diastereomer (1)
$^1$H NMR spectrum (CDCl$_3$, 270 MHz)
δ 1.28–1.96 (m, 7H), 2.28–2.39 (m, 1H), 3.32 (td, 1H, J=4.29 Hz, 10.56 Hz), 3.46
(s, 3H), 4.56 (td, 1H, J=4.29 Hz, 10.56 Hz), 5.71 (br.s, 1H)
Mass spectrum (EI-MS)
m/z 174 (M$^+$), 127, 112, 99, 96, 86, 69, 54, 41
Diastereomer (2)
$^1$H NMR spectrum (CDCl$_3$, 270 MHz)
δ 1.28–1.96 (m, 7H), 2.28–2.39 (m, 1H), 3.48 (s, 3H), 3.53 (m, 1H), 4.77 (m, 1H), 5.71 (br.s, 1H)

Mass spectrum (EI-MS)

m/z 174 (M+), 128, 112, 96, 86, 69, 54, 41

O-Methyl-N-(2-nitrocyclohexyl)hydroxylamine (mixture of diastereomers, 174 mg, 1 mmol) thus obtained was dissolved in 2 ml of N,N-dimethylformamide, and the solution was added dropwise to 3 ml of N,N-dimethylformamide solution containing potassium t-butoxide (224 mg, 2 mmol) at 25° C. over 5 minutes. After completion of the dropwise addition, the mixture was stirred at 25° C. for 30 minutes and allowed to pass through a silica gel short column (eluent: ethyl acetate).

After the solvent was distilled off, the product was isolated and purified by silica gel thin-layer chromatography (eluent: ethyl acetate/hexane=1/1) to give 1-amino-2-nitrocyclohexene (yield: 91%).

EXAMPLE 16

O-Methylhydroxylamine (94 mg, 2 mmol) was added dropwise to N,N-dimethylformamide (1 ml) solution of (E)-3-nitro-β-nitrostyrene (194 mg, 1 mmol) and the mixture was stirred at 25° C. for 20 minutes. Thereafter, water was added and the extraction was conducted with methylene chloride.

The resulting organic layer was dried over anhydrous magnesium sulfate and, after the solvent was distilled off, the product was isolated and purified by silica gel thin-layer chromatography (eluent: ethyl acetate/hexane=1/5).

O-Methyl-N-[1-(3-nitrophenyl)-2-nitroethyl]hydroxylamine (yield: 85%)

$^1$H NMR spectrum (CDCl$_3$, 270 MHz)

δ 3.53 (s, 3H), 4.65 (m, 1H), 4.85–4.98 (m, 2H), 6.00 (br.s, 1H), 7.59 (t, 1H, J=7.92 Hz), 7.72 (m, 1H), 8.21–8.29 (m, 2H)

$^{13}$C NMR spectrum (CDCl$_3$, 68 MHz)

δ 61.92, 62.86, 76.68, 122.66, 123.94, 130.03, 133.82, 138.17, 148.52

Mass spectrum (FD-MS)

m/z 241 (M+)

O-Methyl-N-[1-(3-nitrophenyl)-2-nitroethyl]hydroxylamine (241 mg, 1 mmol) thus obtained was dissolved in 2 ml of N,N-dimethylformamide, and the solution was added dropwise to 3 ml of N,N-dimethylformamide solution containing potassium t-butoxide (224 mg, 2 mmol) at 25° C. over 5 minutes. After the completion of the dropwise addition, the mixture was stirred at 25° C. for 30 minutes and an aqueous saturated ammonium chloride solution was added to the reaction mixture, followed by extraction with methylene chloride.

The resulting organic layer was dried over anhydrous magnesium sulfate and, after the solvent was distilled off, the product was isolated and purified by silica gel thin-layer chromatography (eluent: ethyl acetate/hexane=1/1) to give (Z)-3-nitro-α-amino-β-nitrostyrene (yield: 88%).

What is claimed is:

1. A process for producing β-nitroenamine represented by the formula I:

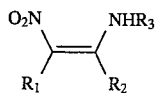

wherein $R_1$ and $R_2$ are the same or different and independently indicate a hydrogen atom or a straight-chain or branched $C_1$–$C_{10}$ alkyl group which may be optionally substituted with at least one group selected from the group consisting of a halogen atom, a lower alkoxy group, an aryloxy group, a hydroxyl group or an aryl group, or an aryl group which may be optionally substituted with at least one group selected from the group consisting of a halogen atom, a lower alkyl group, a lower alkoxy group, an aryl group, an aryloxy group, a nitro group, a cyano group, an acylamino group, a lower dialkylamino group, an arylamino group, a hydroxyl group, an arylsulfonyl group, a mercapto group, a lower alkylthio group or an arylthio group; and $R_1$ and $R_2$ may bond together to form a cycloalkyl or bicycloalkyl group and $R_3$ is a hydrogen atom, a lower alkyl group, a cycloalkyl group or an aralkyl group, which comprises reacting a nitroolefin of the formula II:

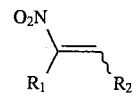

wherein $R_1$ and $R_2$ are as defined above, with a hydroxylamine derivative of the formula III:

wherein $R_3$ is the same as defined above and $R_4$ is a lower alkyl group or an aralkyl group, or a salt thereof in the presence of a base.

2. A process for producing β-nitroenamine represented by the formula I:

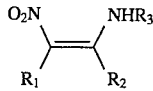

wherein $R_1$, $R_2$ and $R_3$ are as defined in claim 1, which comprises the steps of;

(a) reacting a nitroolefin of the formula II:

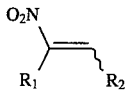

wherein $R_1$ and $R_2$ are as defined in claim 1, with a hydroxylamine derivative of the formula III:

wherein $R_3$ and $R_4$ are as defined above to obtain an N-(β-nitroethyl)hydroxylamine derivative of the formula IV:

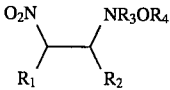

wherein $R_1$, $R_2$, $R_3$ and $R_4$ are as defined in claim 1; and then (b) reacting the resulting derivative IV with a base.

3. A process according to claim 1, wherein the hydroxylamine derivative is O-methylhydroxylamine, O-ethylhydroxylamine, O-t-butylhydroxylamine, O-benzylhydroxylamine or N,O-dimethylhydroxylamine.

4. A process according to claim 1, wherein the hydroxylamine derivative is used in a form of an inorganic acid salt.

5. A process according to claim 4, wherein the inorganic acid is hydrochloric acid.

6. A process according to claim 1, wherein the base is an alkali metal alkoxide or an alkali metal hydroxide.

7. A process according to claim 2, wherein the base is an alkali metal alkoxide or an alkali metal hydroxide.

8. A process according to claim 1, wherein the hydroxylamine derivative or the salt thereof is used in an amount of 0.5 to 6 moles per mole of the nitroolefin.

9. A process according to claim 1, wherein the base is used in an amount of 0.1 to 6 moles per mole of the nitroolefin.

10. A process according to claim 2, wherein the hydroxylamine derivative is O-methylhydroxylamine, O-ethylhydroxylamine, O-t-butylhydroxylamine, O-benzylhydroxylamine or N,O-dimethylhydroxylamine.

11. A process according to claim 2, wherein the hydroxylamine derivative is used in a form of an inorganic acid salt.

12. A process according to claim 11, wherein the inorganic acid is hydrochloric acid.

13. A process according to claim 2, wherein the hydroxylamine derivative or the salt thereof is used in an amount of 0.5 to 6 moles per mole of the nitroolefin.

14. A process according to claim 2, wherein the base is used in an amount of 0.1 to 6 moles per mole of the nitroolefin.

* * * * *